(12) United States Patent
Brisson et al.

(10) Patent No.: US 9,138,297 B2
(45) Date of Patent: Sep. 22, 2015

(54) SYSTEMS AND METHODS FOR CONTROLLING A ROBOTIC SURGICAL SYSTEM

(71) Applicant: Intuitive Surgical Operations, Inc., Sunnyvale, CA (US)

(72) Inventors: Gabriel F. Brisson, Albany, CA (US); Paul W. Mohr, Mountain View, CA (US); Thomas R. Nixon, San Jose, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 410 days.

(21) Appl. No.: 13/756,169

(22) Filed: Jan. 31, 2013

(65) Prior Publication Data

US 2013/0204271 A1  Aug. 8, 2013

Related U.S. Application Data

(60) Provisional application No. 61/594,130, filed on Feb. 2, 2012.

(51) Int. Cl.
*G06F 19/00* (2011.01)
*A61B 19/00* (2006.01)
*A61B 17/00* (2006.01)

(52) U.S. Cl.
CPC ... *A61B 19/2203* (2013.01); *A61B 2017/00477* (2013.01)

(58) Field of Classification Search
USPC .................................................. 700/245–264
See application file for complete search history.

(56) References Cited

U.S. PATENT DOCUMENTS

| | | |
|---|---|---|
| 5,931,832 A | 8/1999 | Jensen |
| 6,246,000 B1 | 6/2001 | Wehrmann et al. |
| 6,331,181 B1 | 12/2001 | Tierney et al. |
| 6,491,701 B2 | 12/2002 | Tierney et al. |
| 6,770,081 B1 | 8/2004 | Cooper et al. |
| 6,817,974 B2 | 11/2004 | Cooper et al. |
| 8,182,469 B2 | 5/2012 | Anderson et al. |
| 8,545,515 B2 | 10/2013 | Prisco et al. |
| 2006/0161137 A1 | 7/2006 | Orban, III |
| 2006/0161138 A1 | 7/2006 | Orban, III |
| 2006/0235436 A1 | 10/2006 | Anderson et al. |
| 2011/0071541 A1 | 3/2011 | Prisco et al. |
| 2011/0071544 A1 | 3/2011 | Steger et al. |
| 2011/0137322 A1 | 6/2011 | Moll et al. |

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

*Primary Examiner* — Bhavesh V Amin

(57) ABSTRACT

A method comprises generating a command to move a surgical robotic manipulator to a predetermined safety configuration and locking the robotic manipulator in the safety configuration in response to receiving the command. The method further comprises detecting if a mock instrument has been mounted on the robotic manipulator when the robotic manipulator is in the safety configuration. If the mock instrument is detected, an override command is generated to unlock the robotic manipulator from the safety configuration.

22 Claims, 9 Drawing Sheets

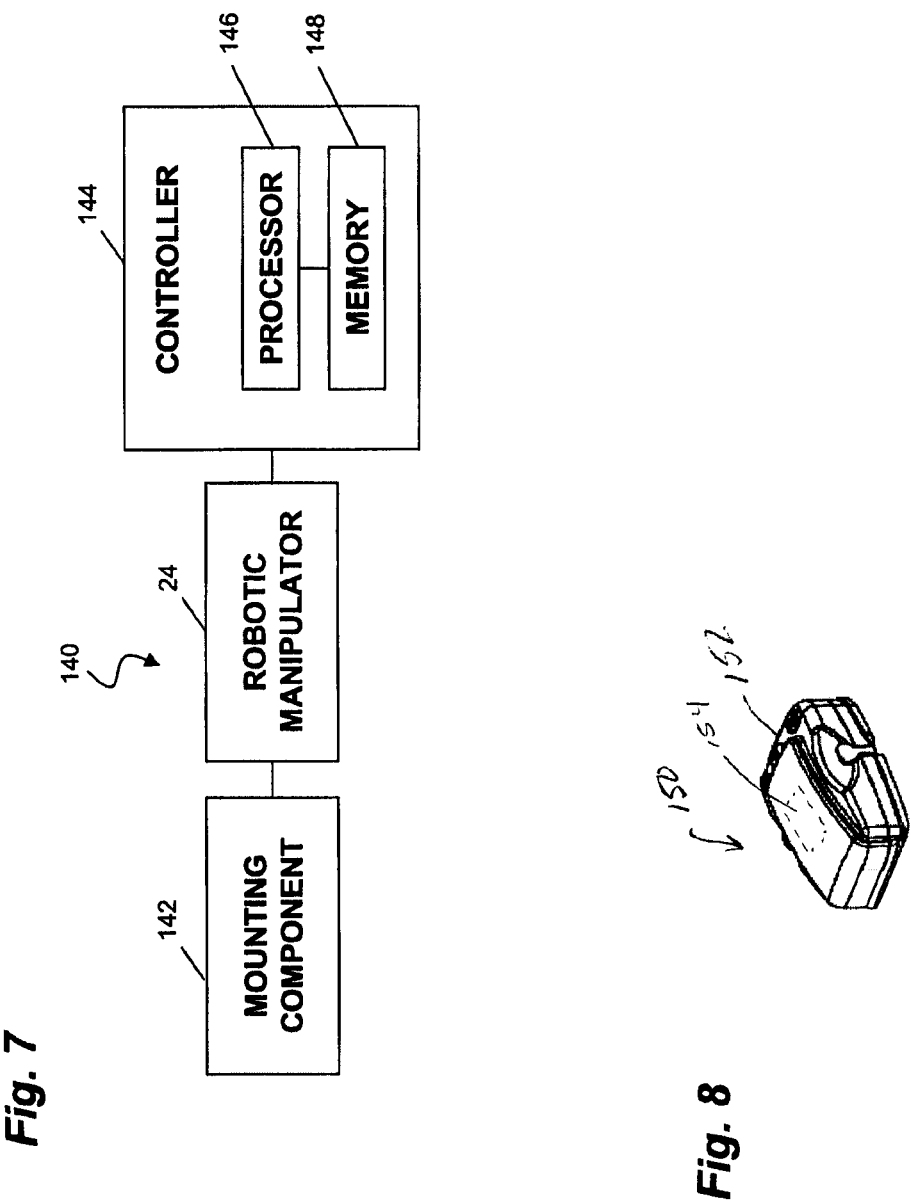

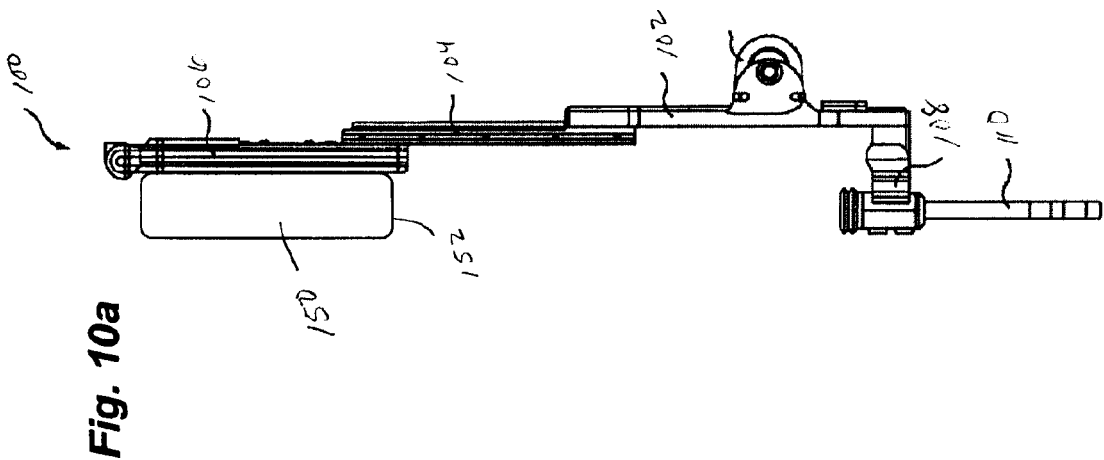

SYSTEMS AND METHODS FOR CONTROLLING A ROBOTIC SURGICAL SYSTEM

CROSS REFERENCE TO RELATED APPLICATIONS

The present application claims priority to and the benefit of U.S. Provisional Patent Application No. 61/594,130, filed Feb. 2, 2012, which is hereby incorporated by reference herein in its entirety.

FIELD

The present disclosure is directed to surgical systems and methods for use in minimally invasive robotically assisted surgery, and more particularly to systems and methods for the safe, accurate, and efficient preparation of a robotic surgical system for operation.

BACKGROUND

Minimally invasive medical techniques are intended to reduce the amount of extraneous tissue that is damaged during diagnostic or surgical procedures, thereby reducing patient recovery time, discomfort, and deleterious side effects. Minimally invasive robotic surgical or telesurgical systems have been developed to increase a surgeon's dexterity and to avoid some of the limitations on traditional minimally invasive techniques. In telesurgery, the surgeon uses some form of remote control, e.g., a servomechanism or the like, to manipulate surgical instrument movements, rather than directly holding and moving the instruments by hand. In telesurgery systems, the surgeon can be provided with an image of the surgical site at the surgical workstation. While viewing a two or three dimensional image of the surgical site on a display, the surgeon performs the surgical procedures on the patient by manipulating master control devices, which in turn control motion of the servomechanically operated instruments.

In robotically-assisted telesurgery, the surgeon typically operates a master controller to control the motion of surgical instruments at the surgical site from a location that may be remote from the patient (e.g., across the operating room, in a different room, or a completely different building from the patient). The master controller usually includes one or more hand input devices, such as hand-held wrist gimbals, joysticks, exoskeletal gloves or the like, which are operatively coupled to the surgical instruments that are releasably coupled to a patient side surgical manipulator ("the slave"). The master controller controls the instrument's position, orientation, and articulation at the surgical site. The slave is an electro-mechanical assembly which includes a plurality of arms, joints, linkages, servo motors, etc. that are connected together to support and control the surgical instruments. In a surgical procedure, the surgical instruments (including an endoscope) may be introduced directly into an open surgical site or more typically through cannulas into a body cavity.

For minimally invasive surgical procedures, the surgical instruments, controlled by the surgical manipulator, may be introduced into the body cavity through a single surgical incision site or through multiple closely spaced incision sites on the patient's body. These minimally invasive procedures may present multiple challenges. For example, the preparation of a surgical site is often a manual, time consuming process complicated by the convergence of multiple arms and linkages of the surgical manipulator into a very small surgical area. Similar challenges arise during instrument exchange and at the conclusion of surgical procedures. Improved systems and methods are needed to improve efficiency during these types of transition procedures while maintaining safety and accuracy throughout the surgery.

SUMMARY

The embodiments of the invention are summarized by the claims that follow below.

In one embodiment, a method comprises generating a command to move a surgical robotic manipulator to a predetermined safety configuration and locking the robotic manipulator in the safety configuration in response to receiving the command. The method further comprises detecting if a mock instrument has been mounted on the robotic manipulator when the robotic manipulator is in the safety configuration. If the mock instrument is detected, an override command is generated to unlock the robotic manipulator from the safety configuration.

In another embodiment, A robotic surgical system comprises a surgical robotic manipulator and a mock instrument adapted to mount to the robotic manipulator. The system further comprises a control system adapted to generate a command to lock the robotic manipulator in a predetermined safety configuration and detect if the mock instrument is mounted to the robotic manipulator. The control system also generates a command to unlock the robotic manipulator from the safety configuration if the mock instrument is detected and generate a command to allow the unlocked robotic manipulator to move to a second configuration.

A method of controlling a surgical robotic system comprises detecting if a mock instrument has been mounted to a robotic manipulator of the robotic system. The method further comprises receiving information about the mock instrument in response to the detection of a mock instrument. The method further comprises generating a command to move the robotic manipulator to a predetermined configuration, in response to the received information.

BRIEF DESCRIPTIONS OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

FIG. 7 is a schematic diagram illustrating interactions in the robotic surgical system.

FIG. 8 is a perspective view of a mock instrument for use with the manipulator of FIG. 3.

FIGS. 10a and 10b are side views of the insertion spar and the mock instrument in an expanded configuration and in a collapsed configuration, respectively.

DETAILED DESCRIPTION

In the following detailed description of the embodiments of the invention, numerous specific details are set forth in order to provide a thorough understanding of the disclosed embodiments. However, it will be obvious to one skilled in the art that the embodiments of this disclosure may be practiced without these specific details. In other instances well known methods, procedures, components, and circuits have not been described in detail so as not to unnecessarily obscure aspects of the embodiments of the invention.

Figure 1:
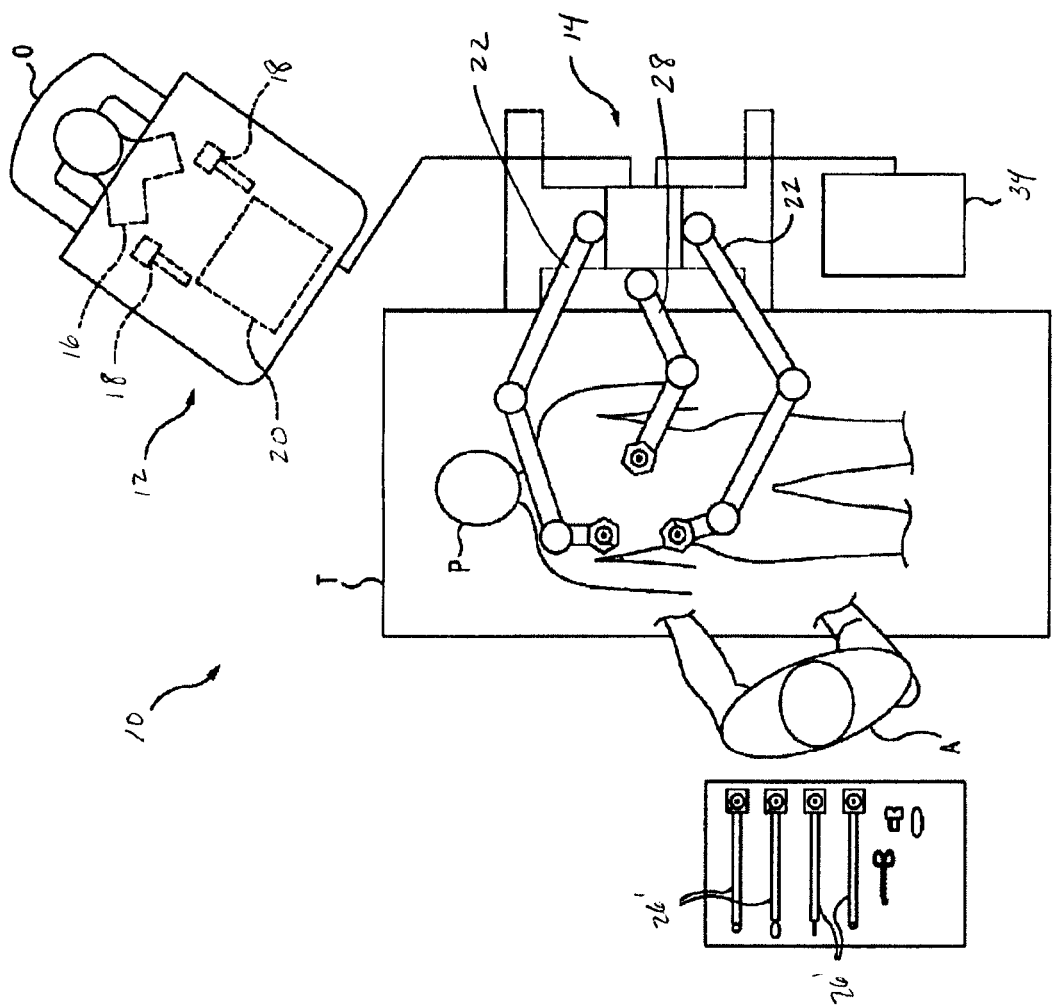
FIG. 1 is a schematic plan view of a portion of an operating theater illustrating a robotic surgical system, including a master surgeon console or workstation for inputting a surgical procedure and a robotic manipulator system for robotically moving surgical instruments at a surgical site within a patient.

FIG. 1 is a schematic plan view of a portion of an operating theater illustrating a robotic surgical system 10, including a master surgeon console or workstation 12 for inputting a surgical procedure and a robotic manipulator system 14 for robotically moving surgical instruments at a surgical site within a patient P. The robotic surgical system 10 is used to perform minimally invasive robotic surgery. One example of a robotic surgical system that can be used to implement the systems and techniques described in this disclosure is the da Vinci® Surgical System (specifically, a Model IS3000, marketed as the da Vinci® Si™ HD™ Surgical System), manufactured by Intuitive Surgical, Inc. of Sunnyvale, Calif. Those skilled in the art will understand that the inventive aspects disclosed herein may be embodied and implemented in various ways, including robotic and non-robotic embodiments and implementations. Implementations on da Vinci® Surgical Systems (e.g., the Model IS3000; the Model IS2000, marketed as the da Vinci® S™ HD™ Surgical System) are merely exemplary and are not to be considered as limiting the scope of the inventive aspects disclosed herein. Further details of these exemplary robotic surgical systems are provided, for example, in U.S. Pat. No. 6,246,200 and pending U.S. patent application Ser. No. 12/618,583, the full disclosures of which are incorporated herein by reference.

The system 10 is used by a system operator O (generally a surgeon) who performs a minimally invasive surgical procedure on a patient P lying on an operating table T. The system operator O sees images presented on a display 16 and manipulates one or more input devices or masters 18 at the master console 12. In response to the surgeon's input commands, a computer system 20 of console 12 effects servomechanical movement of surgical instruments coupled to the robotic patient-side manipulator system 14 (a cart-based system in this example).

Computer system 20 will typically include data processing hardware and software, with the software typically comprising machine-readable code. The machine-readable code will embody software programming instructions to implement some or all of the methods described herein. While computer system 20 is shown as a single block in the simplified schematic of FIG. 1, the system may comprise a number of data processing circuits (e.g., on the surgeon's console 12 and/or on the patient-side manipulator system 14), with at least a portion of the processing optionally being performed adjacent an input device, a portion being performed adjacent a manipulator, and the like. Any of a wide variety of centralized or distributed data processing architectures may be employed. Similarly, the programming code may be implemented as a number of separate programs or subroutines, or may be integrated into a number of other aspects of the robotic systems described herein. In one embodiment, computer system 20 may support wireless communication protocols such as Bluetooth, IrDA, HomeRF, IEEE 802.11, DECT, and Wireless Telemetry.

Figure 2:
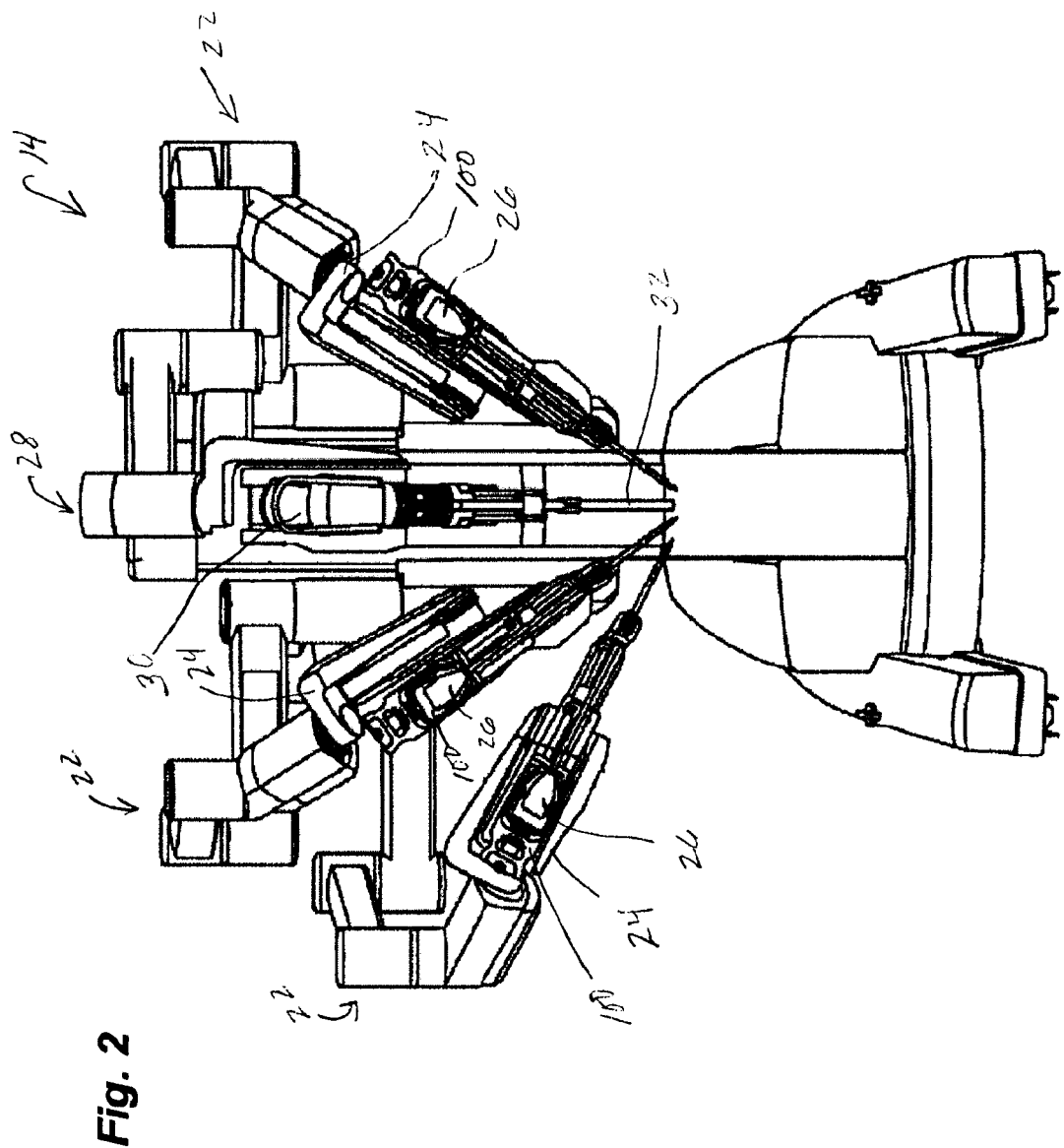
FIG. 2 is a front elevation view of a patient side manipulator in a robotic surgical system.

Referring now to FIG. 2, in one example, manipulator system 14 includes at least four robotic manipulator assemblies. Three linkages 22 (mounted at the sides of the cart in this example) support and position manipulators 24, with linkages 22 in general supporting a base of the manipulators 24 at a fixed location during at least a portion of the surgical procedure. Manipulators 24 move surgical instruments 26 for robotic manipulation of tissues. One additional linkage 28 (mounted at the center of the cart in this example) supports and positions manipulator 30 which controls the motion of an endoscope/camera probe 32 to capture an image (for example, stereoscopically) of the internal surgical site. The fixable portion of positioning linkages 22, 28 of the patient-side system is sometimes referred to herein as a "set-up arm."

Referring again to FIG. 1, in one example, the image of the internal surgical site is shown to operator O by the stereoscopic display 16 in surgeon's console 12. The internal surgical site is simultaneously shown to assistant A by an assistance display 34.

Assistant A assists in pre-positioning manipulator assemblies 24 and 30 relative to patient P using set-up linkage arms 22, 28; in swapping instruments 26 from one or more of the surgical manipulators for alternative surgical tools or instruments 26'; in operating related non-robotic medical instruments and equipment; in manually moving a manipulator assembly so that the associated tool accesses the internal surgical site through a different aperture; and the like.

In general terms, the linkages 22, 28 are used primarily during set-up of patient-side system 14, and typically remain in a fixed configuration during at least a portion of a surgical procedure. Manipulators 24, 30 each comprise a driven linkage which is actively articulated under the direction of surgeon's console 12. Although one or more of the joints of the set-up arm may optionally be driven and robotically controlled, at least some of the set-up arm joints may be configured for manual positioning by assistant A.

For convenience, a manipulator such as manipulator 24 that is supporting a surgical instrument 26 used to manipulate tissues is sometimes referred to as a patient-side manipulator (PSM), while a manipulator 30 which controls an image capture or data acquisition device such as endoscope 32 may be referred to as an endoscope-camera manipulator (ECM). The manipulators may optionally actuate, maneuver and control a wide variety of instruments or tools, image capture devices, and the like which are useful for surgery. Some of the manipulators include a telescopic insertion spar 100. In other embodiments, all of the manipulators may include a telescopic insertion spar 100. Telescopic insertion spar 100 allows for movement of the mounted instruments 26.

Figure 3:
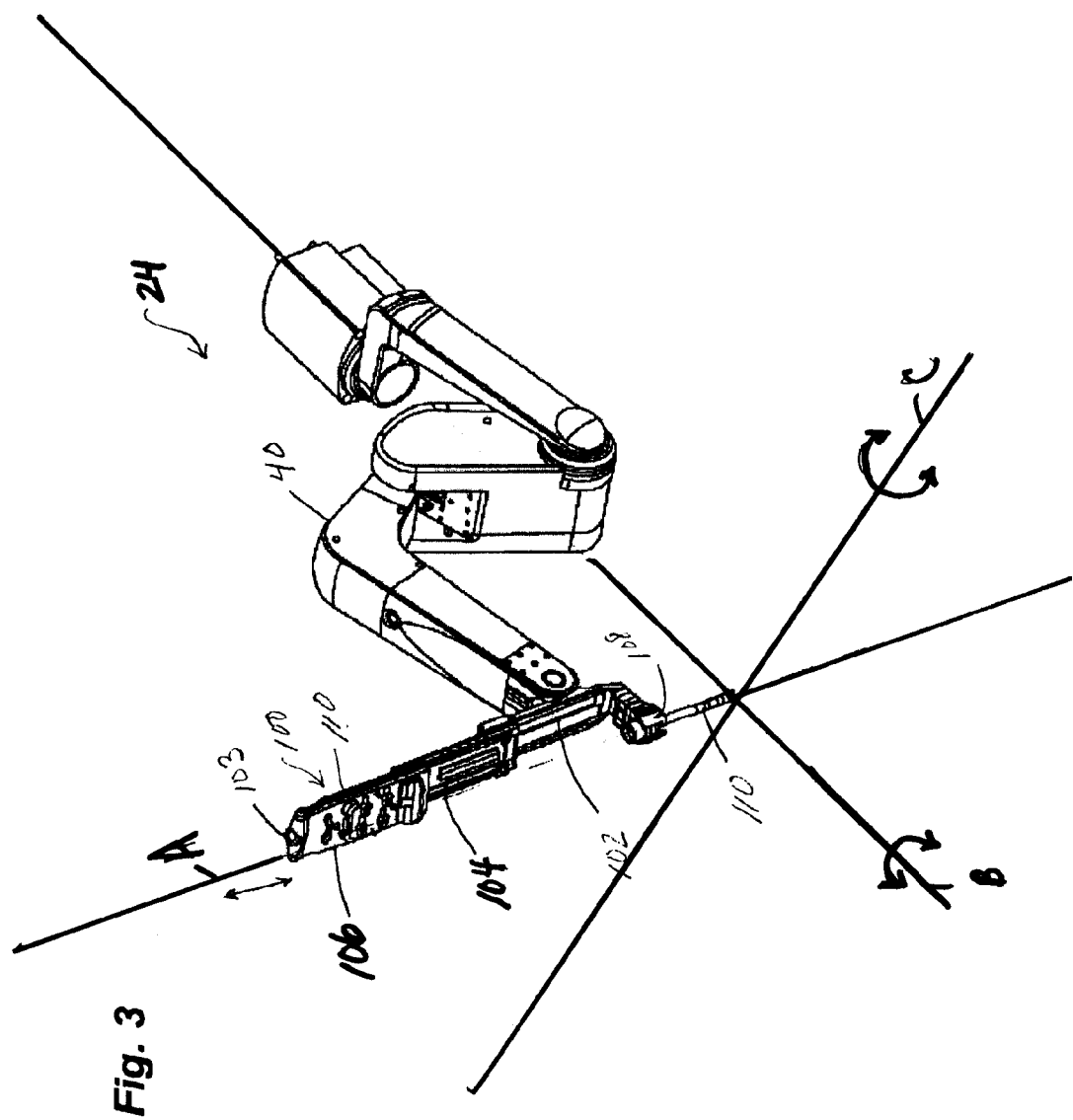
FIG. 3 is a perspective view of a manipulator including a telescopic insertion spar.

FIG. 3 illustrates a perspective view of a manipulator 24 including a telescopic insertion spar 100. In this example, the insertion spar 100 is comprised of a 3-stage telescopic spar including three links movably coupled to one another via rails, pulleys, and cables, with the links narrowing in width or form factor moving from the proximal link toward the distal link. The manipulator 24 includes a manipulator arm 40, and telescopic insertion spar 100 operably coupled to a distal end of arm 100 in accordance with one embodiment of the present disclosure. Telescopic insertion spar 100 includes a first link or base link 102, a second link or idler link 104 operably coupled to base link 102, and a third link or carriage link 106 operably coupled to idler link 104.

Base link 102 is operably coupled to a distal end of arm 40, and in one example has an accessory mount 108 attached to a distal end of base link 102. An accessory 110, such as a cannula, may be mounted onto accessory mount 108. An example of applicable accessory mount and accessories are disclosed in pending U.S. application Ser. No. 11/240,087, filed Sep. 30, 2005, the full disclosure of which is incorporated by reference herein for all purposes. Examples of accessory mounts and accessories, including curved cannulas and cannula mounts are disclosed in pending U.S. application Ser. No. 12/618,549, filed Nov. 13, 2009, the full disclosure of which is incorporated by reference herein for all purposes. Such curved cannulas and cannula mounts may be particularly applicable for single incision minimally invasive surgical procedures.

Carriage link 106 includes an instrument interface 111 for operably coupling to the instrument 26 and controlling the depth of the instrument inside a patient. The instrument 26 may couple directly to the interface 111 or may, alternatively, couple to the interface 111 via a sterile adaptor, which in turn is operably coupled to the interface 111. The sterile adapter may be part of a drape that may be draped over the robotic surgical system, and in particular the manipulator system, to establish a sterile barrier between the non-sterile PSM arms and the sterile field of the surgical procedure. An example of an applicable drape and adaptor is disclosed in pending U.S. application Ser. No. 11/240,113 filed Sep. 30, 2005 and U.S. application Ser. No. 11/314,040 filed Dec. 20, 2005, the full disclosures of which are incorporated by reference herein for all purposes.

Idler link 104 is movably coupled between base link 102 and carriage link 106 to allow the links 102, 104, and 106 to move relative to one another along a lengthwise axis A in a telescoping fashion.

Figure 5:
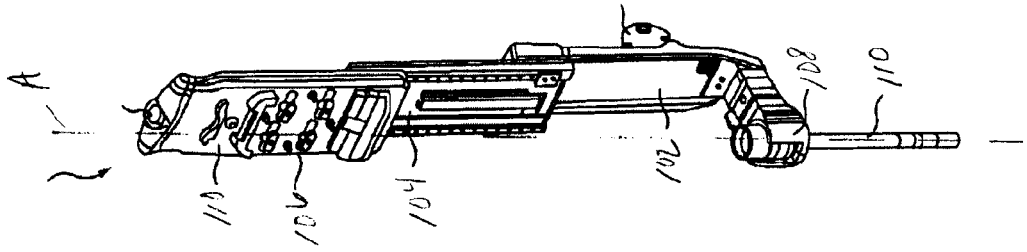
FIG. 5 is a perspective view of a telescopic insertion spar in an expanded configuration.
Figure 4:
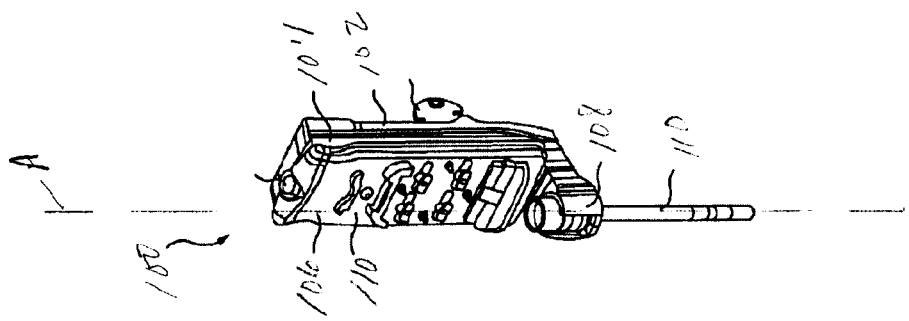
FIG. 4 is a perspective view of a telescopic insertion spar in a collapsed configuration.

FIGS. 4 and 5 are perspective views of the insertion spar 100, accessory mount 108 (e.g., a cannula mount), and an accessory 110 (e.g., a cannula) but not including an instrument or an instrument adaptor. The insertion spar 100 is telescoped from a collapsed configuration in FIG. 4 to a fully expanded configuration in FIG. 5. In the collapsed configuration of FIG. 4, links 102, 104, 106 are collapsed to approximately the same position along the lengthwise axis A. In the expanded configuration of FIG. 5, link 106 is positioned proximally of the link 102 along the lengthwise axis A. In one embodiment, the carriage link 106 may translate a distance of about 11.5 inches between the collapsed configuration and the expanded configuration, while the idler carriage 104 may translate a distance of about 5.75 inches. The insertion spar 100 may also be configured in various intermediate configurations between the expanded and collapsed configurations.

The insertion spar 100 provides a range of motion to an attached instrument 26 through the use of cables extending at least between the links of the spar. The cables are a component of a transmission system that may also include drive pulleys, capstans, idler pulleys, and/or output pulleys, which are driven by electric motors. For example, a pulley bank may be located on an underside of base link 102 for passing cables between insertion spar 100 and manipulator arm 40 of manipulator 24. A plurality of motion feed-throughs, in addition to other elements, may also be provided for transferring motion.

The drive assembly may further include a plurality of drive motors coupled to the arm for rotation therewith. Yaw and pitch motors control the motion of the arm 40 about the B axis and the C axis, respectively, and drive motors control further motion of the surgical instrument. In one embodiment, drive motors are mounted proximally in the arm 40 to control four degrees of freedom of the tool mounted distally on the arm. Also, a proximally mounted motor controls the insertion position of the instrument distally on the arm 40 (along the A axis). The drive motors will preferably be coupled to encoders and potentiometers (not shown) to enable the servomechanism. Embodiments of the drive assembly, arm, and other applicable parts are described for example in U.S. Pat. Nos. 6,331,181, 6,491,701, and 6,770,081, the full disclosures of which (including disclosures incorporated by reference therein) are incorporated herein by reference for all purposes. The manipulator arm and the drive assembly may also be used with a broad range of positioning devices. A more complete description of a remote center positioning device can be found in U.S. patent application Ser. No. 08/504,301, filed Jul. 20, 1995, now U.S. Pat. No. 5,931,832, the complete disclosure of which is incorporated herein by reference for all purposes.

Instruments 26 and endoscope 32 may be manually positioned when setting up for a surgical procedure, when reconfiguring the manipulator system 14 for a different phase of a surgical procedure, when removing and replacing an instrument with an alternate instrument 26', and the like. During such manual reconfiguring of the manipulator assembly by assistant A, the manipulator assembly may be placed in a different mode than is used during master/slave telesurgery, with the manually repositionable mode sometimes being referred to as a clutch mode. The manipulator assembly may change between the tissue manipulation mode and the clutch mode in response to an input such as pushing a button or switch on manipulator 24 (e.g., a clutch button/switch 103 in FIG. 3), or some other component to the manipulator assembly, thereby allowing assistant A to change the manipulator mode.

Figure 6A:
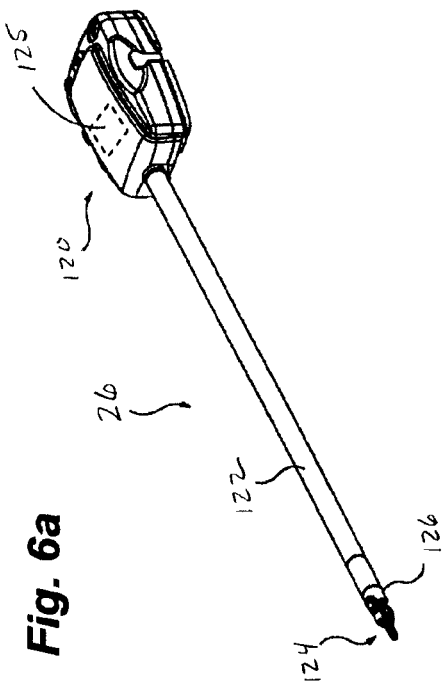
FIGS. 6a and 6b are perspective views of embodiments of surgical instruments for use with the manipulator of FIG. 3.
Figure 6B:
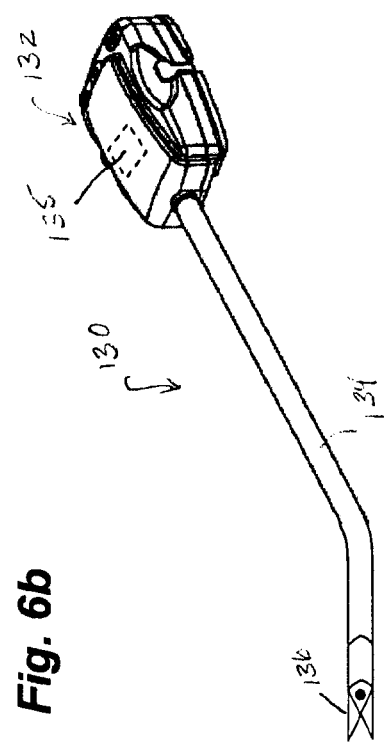

FIGS. 6a and 6b are perspective views of embodiments of surgical instruments for use with the insertion spar 100. FIG. 6a illustrates an articulated surgical instrument 26. Instrument 26 has a instrument mounting component 120 which interfaces with the instrument interface 111 of the insertion spar 100, generally providing a quick release mounting engagement through a sterile adapter, an example of which is disclosed in U.S. patent application Ser. No. 11/314,040, filed Dec. 20, 2005, and U.S. patent application Ser. No. 11/395, 418, filed Mar. 31, 2006, which are incorporated by reference herein for all purposes. Instrument 26 includes a rigid elongated shaft 122 supporting an end effector 124 distally of the instrument mounting component 120. Instrument mounting component 120 accepts and transmits drive signals or drive motion between the manipulator 24 and the end effector 124. An articulated wrist 126 may provide two degrees of freedom of motion between end effector 124 and shaft 122, and the shaft may be rotatable relative to instrument mounting component 120 about the axis of the shaft so as to provide the end effector 124 with three orientational degrees of freedom within the patient's body.

The instrument mounting component 120 houses circuitry including a memory structure 125 that stores identifying information about the instrument 26 such as a part number, a serial number, an end-of-life indicator, manufacturing information, information about the physical characteristics (e.g., size) of the instrument 26, and/or other information about the instrument 26. In one embodiment, the memory structure comprises a DS2505 memory available from Maxim Integrated Products, Inc. of Sunnyvale, Calif. In another embodiment, the memory structure may include a radio frequency identification (RFID) antenna and chip. When the component 120 is coupled to the instrument interface 111, the computer system 20 detects the presence of the component and uses the information stored in the memory structure 125 to configure the manipulator 24 to use the instrument 26.

FIG. 6b illustrates a flexible surgical instrument 130. Instrument 130 has an instrument mounting component 132 which interfaces with the instrument interface 111 of the insertion spar 100, generally providing a quick release mounting engagement through a sterile adaptor. Instrument 130 includes a flexible elongated shaft 134 supporting an end effector 136 distally of the instrument mounting component 132. End effector 136 illustratively operates with a single DOF (e.g., closing jaws). A wrist to provide one or more end effector DOF's (e.g., pitch, yaw; see e.g., U.S. Pat. No. 6,817,974 (filed Jun. 28, 2002) (disclosing surgical tool having positively positionable tendon-actuated multi-disk wrist joint), which is incorporated herein by reference) is optional and is not shown. Many instrument implementations do not include such a wrist. Omitting the wrist simplifies the number of actuation force interfaces between manipulator 24 and instrument 130, and may reduce instrument complexity and dimensions. Further examples of flexible surgical instruments are described in U.S. patent Ser. No. 12/618,608, filed Nov. 13, 2009, the full disclosure of which is incorporated by reference herein for all purposes. The instrument mounting component 132 houses circuitry including a memory structure 135 that stores identifying information about the instrument 130.

The surgical instrument 26, 130 may include a variety of articulated end effectors, such as jaws, scissors, graspers, needle holders, micro-dissectors, staple appliers, tackers, suction irrigation tools, and clip appliers, that may be driven by wire links, eccentric cams, push-rods, or other mechanisms. In addition, the surgical instruments may comprise a non-articulated instrument, such as cutting blades, probes, irrigators, catheters or suction devices. Alternatively, the surgical tool may comprise an electrosurgical probe for ablating, resecting, cutting or coagulating tissue. Examples of applicable adaptors, tools or instruments, and accessories are described in U.S. Pat. Nos. 6,331,181, 6,491,701, and 6,770,081, the full disclosures of which (including disclosures incorporated by reference therein) are incorporated by reference herein for all purposes. Applicable surgical instruments are also commercially available from Intuitive Surgical, Inc. of Sunnyvale, Calif.

FIG. 7 is a schematic diagram illustrating a control system 140 of the robotic surgical system 10 for recognizing a mounting component 142 mounted to the manipulator 24 and permitting rearrangement of the manipulator in response to the recognition of the mounting component. The mounting component 142 may be, for example, an instrument mounting component 125, 132 or a mounting component of a mock instrument as will be described below. The control system 140 includes a controller 144, which is part of the computer system 20. Controller 144 includes a processor 146 and a memory 148. The processor 146 typically includes analog and digital input/output boards, interface boards, and various controller boards. The memory 148 may be any type of volatile or non-volatile storage device including, for example, a re-programmable "flash" memory. The controller 144 detects a component 142 coupled to the robotic manipulator 24 and determines whether the component 142 is a recognized component. The determination of whether the component 142 is recognized may include comparing identification information from the component 142 with other information stored in the controller memory 148, stored in other memory devices of the computer system 20, or stored on networked computers connected via wired or wireless communication links. If the component 142 is a recognized component, the stored information associated with the component 142 may used by the controller 142 to arrange the robotic manipulator 24 in a predetermined configuration or may be used to trigger the manipulator to enter an operator-controlled "float" status in which the manipulator, including the insertion spar 100, may be manually arranged by the operator.

During the course of a surgical procedure using the robotic surgical system 10, a surgical instrument is often coupled to the insertion spar. However, there are occasions when a surgical instrument is removed from the insertion spar 100. For example, the insertion spar 100 may not carry an instrument during the initial manipulator preparation and cannula docking procedures, during tool exchanges, or during concluding procedures such as cannula removal. As a safety feature of the system 10, the insertion spar 100 will be locked in a predetermined safety configuration during the removal of a surgical instrument from the spar or will be moved to the predetermined safety configuration immediately upon the removal of the surgical instrument. The spar 100 will remain locked in this safety configuration until another surgical instrument is coupled to the spar. In the safety configuration, the links 102, 104, 106 of the spar 100 are positioned such that the end effector of a surgical instrument being coupled to or decoupled from the insertion spar will be held a safe distance from the patient anatomy to prevent injury. The safety configuration may be the expanded configuration of FIG. 5 or any other configuration of the insertion spar 100 that positions the end effector of an attached surgical instrument a safe distance from the patient anatomy throughout the coupling and decoupling of a surgical instrument. For example, the safety configuration may prevent the end effector of an attached surgical instrument from inserting distally beyond the accessory mount or beyond the distal end of an accessory, such as a cannula, attached to the accessory mount. The spar will also be locked in the safety configuration if certain accessories, such as a cannula 110, are not docked to the insertion spar.

While the safety configuration desirably limits the insertion of an attached surgical instrument, the expansion or partial expansion of the links 102, 104, 106 may create a challenge when trying to position multiple manipulator arms, with expanded insertion spars, around a single surgical incision or around multiple closely spaced incisions. During procedures in which the manipulator arms may be repositioned, such as the initial manipulator preparation, cannula docking, or cannula removal, a collapsed configuration of the insertion spar (See FIG. 4) may be preferred to allow for the convergence of multiple manipulator arms around a small area. In one embodiment, the collapsed configuration may be achieved by controlling the insertion spar to move to a predetermined collapsed configuration. In another embodiment, a collapsed or partially collapsed configuration may be achieved by changing the control of the manipulator arms to a floating configuration in which a user can manually adjust both the insertion spar and the manipulator arm during the repositioning procedure. Examples of the floating configuration are described in U.S. patent application Ser. No. 12/959,704 which is fully incorporated by reference herein for all purposes.

Arranging the insertion spars on each manipulation arm in a collapsed or partially collapsed configuration may, for example, simplify and thus expedite the process of cannula docking. With the insertion spars in a collapsed configuration, the surgeon or assistant has more maneuvering room to dock the cannulas to respective cannula mounts and to position the cannulas in one or more patient incisions.

To safely override the safety configuration of the insertion spar and allow the insertion spar to collapse without an attached surgical instrument and without a docked cannula, a mock instrument 150 is used to prevent the coupling of a surgical instrument to the insertion spar after the spar is in a collapsed or partially collapsed configuration. FIG. 8 illustrates one such mock instrument 150. Mock instrument is a non-surgical device that does not include a surgical end effector that extends into a surgical site. In certain embodiments, the mock instrument does not include a shaft or other projections. In alternative embodiments, the mock instrument may include non-surgical projections such as cannula alignment pins or other mechanical or optical positioning or alignment features. Generally, a distal end of a mock instrument will not extend distally beyond a distal end of the insertion spar 100 or a cannula 110 mounted to the insertion spar. Mock instrument 150 includes a mounting component 152 configured to couple with the instrument interface 111. The mounting component 152 houses circuitry including a memory structure 154 that stores identifying information about the mock instrument 150 such as a part number, a serial number, manufacturing information, information about the physical characteristics (e.g., size) of the mock instrument 150, and/or other information about the mock instrument. In one embodiment, the memory structure comprises a Maxim DS2505 memory. In another embodiment, the memory structure may include an RFID antenna and chip. When the mock instrument 150 is coupled to the instrument interface 111, the controller 144 detects the presence of the mock instrument and determines that it is safe to override the safety configuration of the insertion spar 100. This determination triggers the insertion spar 100 to become unlocked from the safety configuration.

Figure 9B:
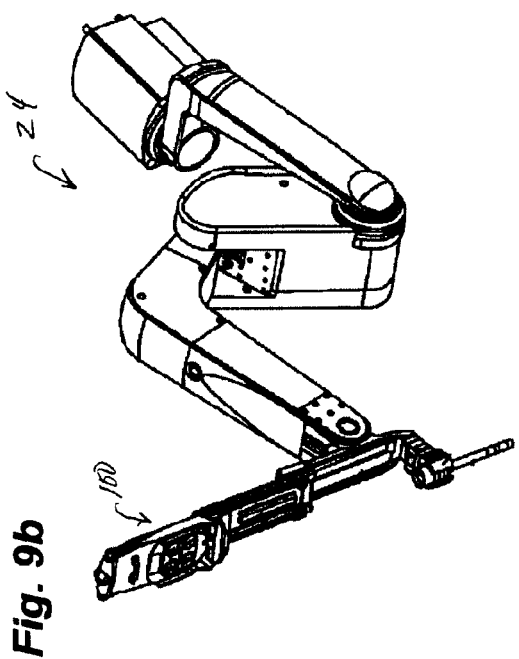
FIGS. 9a-9d are perspective views of the manipulator and insertion spar of FIG. 3 in use with the surgical instrument of FIG. 6a or the mock instrument of FIG. 8.
Figure 9D:
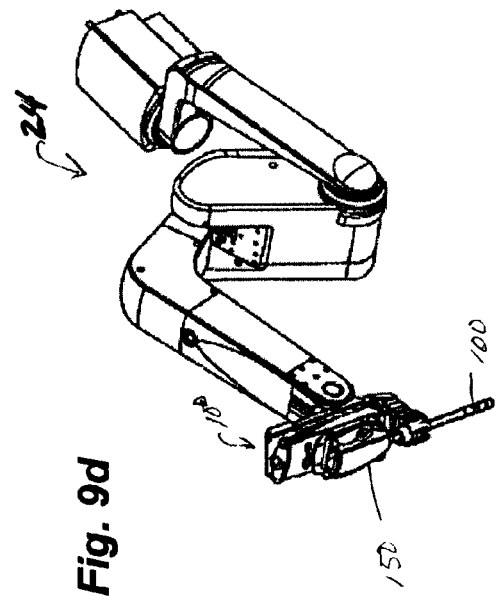
Figure 9A:
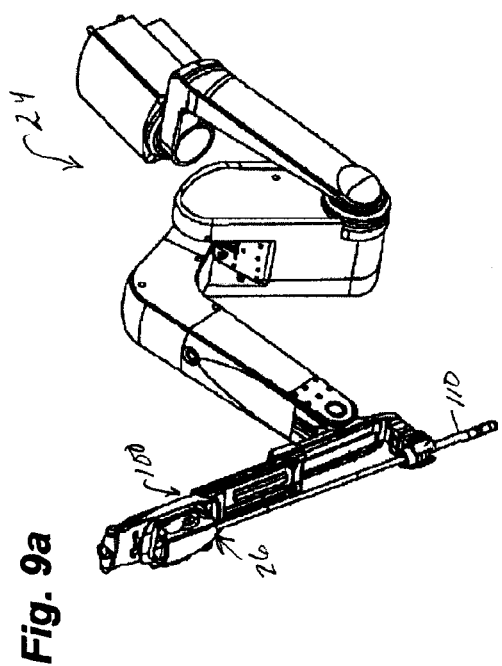

FIGS. 9a-9d are perspective views of the manipulator 24 and insertion spar 100 illustrating the movement of the insertion spar 100 from the safety configuration to the collapsed configuration. FIG. 9a illustrates an instrument 26 coupled to the insertion spar 100. The spar 100 is moved to a safety configuration, such as a fully expanded configuration, in which the end effector of the instrument 26 is housed safely within the cannula 110, out of direct contact with a patient anatomy. With the insertion spar in this safety configuration, the instrument 26 may be safely decoupled from the insertion spar 100.

FIG. 9b illustrates the insertion spar 100 without an attached instrument. The controller 144 detects the absence of an attached instrument and locks the insertion spar 100 in this expanded safety configuration until another recognized component is coupled to the insertion spar 100. Locking the insertion spar 100 in the safety configuration serves to prevent a user from collapsing the insertion spar and then inadvertently attaching an instrument to the spar. An instrument attached to the insertion spar 100 in a collapsed configuration has the potential to collide with a patient anatomy and injure the patient.

Figure 9C:
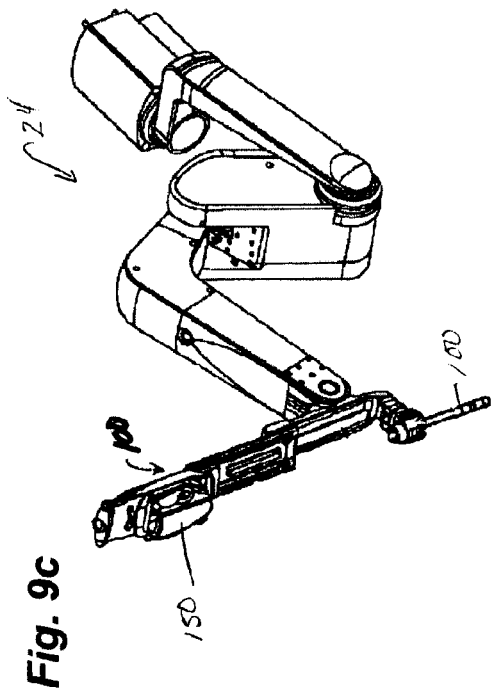

FIG. 9c illustrates the mock instrument 150 coupled to the insertion spar 100. The controller 144 detects the mock instrument 150 and, if it is recognized, overrides the safety lock. In one embodiment, the detection of the mock instrument 150 may trigger the controller to command the insertion spar to move to the predetermined collapsed configuration as shown in FIG. 9d. In an alternative embodiment the detection of the mock instrument 150 may trigger the controller to unlock insertion spar and allow the insertion spar to float such that an operator, such as a surgeon or assistant, may collapse or expand the insertion spar as desired during preparation, transition, or concluding procedures associated with the minimally invasive surgical procedure. In another alternative, an operator may manually collapse or partially collapse the insertion spar by activating the clutch button 103.

FIGS. 10a and 10b are side views of the insertion spar 100 and the mock instrument 150 in an expanded configuration and in a collapsed configuration, respectively. The mock instrument may have any size or shape that will prevent the mounting of a surgical instrument mounting component to the instrument interface 111 of the insertion spar 100. In this embodiment, the mock instrument 150 may have a block shape, without any extensions or operable features. The mock instrument 150 includes a distal end portion 152 that remains proximal of the accessory mount 108 located at the distal end of the insertion spar 100. As shown in FIG. 10b, the shape of the mock instrument 150 in this embodiment serves to both obstruct access to the interface 111 and also restrict access to the opening of cannula 110. In alternative embodiments, a mock instrument may have extensions, such as a plug sized to extend partially through the cannula 110, identifying marks, or other safety-related features. Generally, any extensions, shafts, or other projections of the mock instruments are sized to extend only partially into the cannula without extending distally beyond the distal end of the cannula.

Figure 11:
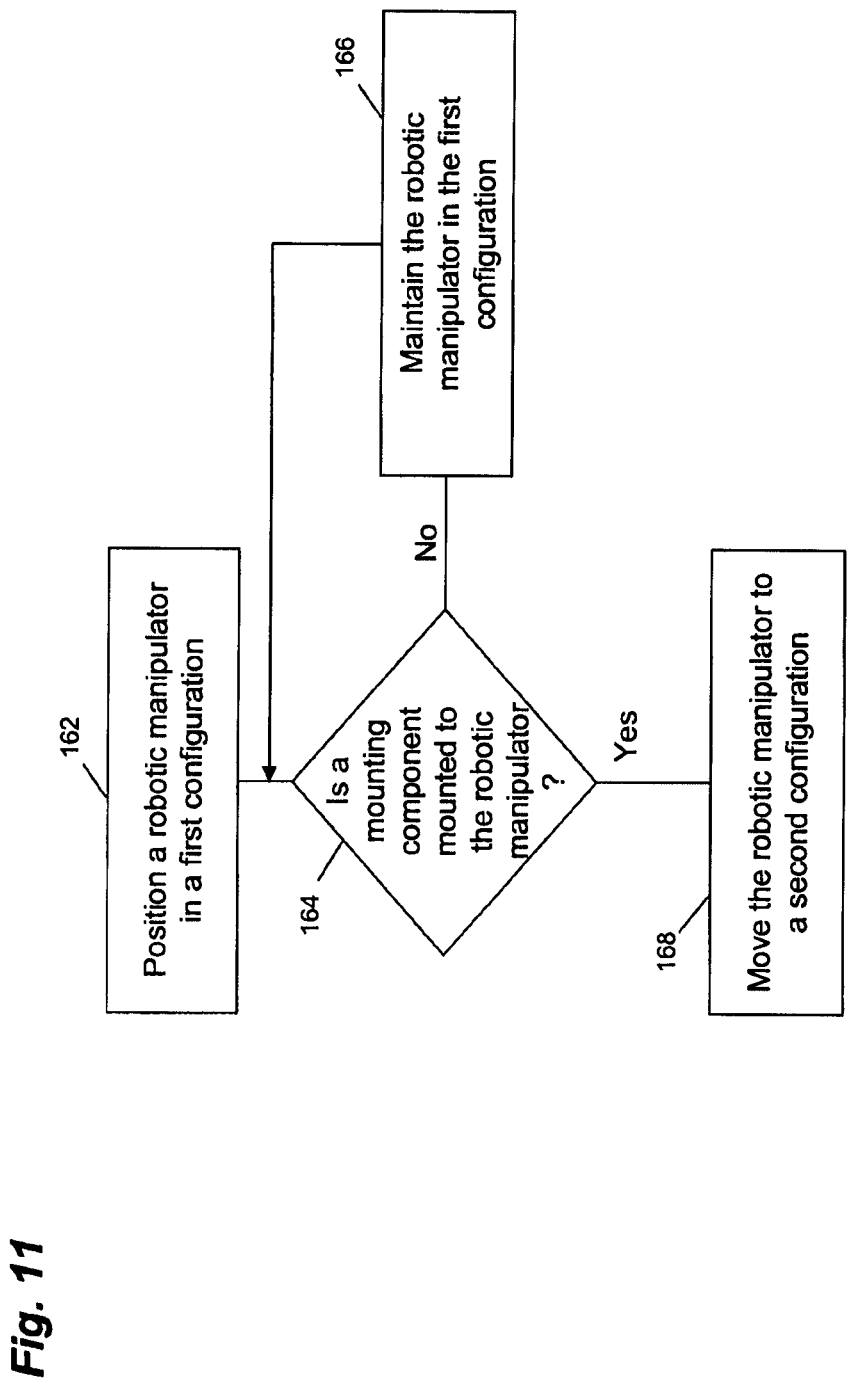
FIG. 11 is a flow chart illustrating one embodiment for operating the robotic surgical system of FIG. 1.

Referring now to FIG. 11, a flow chart 160 illustrates one embodiment for operating the robotic surgical system 10 of FIG. 1. At step 162, the robotic manipulator 24 is arranged in a first configuration. More specifically, the controller 144 generates a command to move the insertion spar 100 to a predetermined safety configuration, such as the extended configuration of FIG. 5. Once positioned in the safety configuration, the insertion spar 100 is locked to prevent linear motion of the insertion spar along the axis A.

At step 164, the system 10 detects if a mounting component, such as the mock instrument 150, has been mounted to the manipulator 24 when the manipulator is positioned in the first configuration. More specifically, the controller 144 detects if a recognized mock instrument has been mounted to the insertion spar 100. Recognizing the mock instrument may also include receiving identifying information about the mounting component.

At step 166, if a recognized mounting component is not mounted to the manipulator 24, the manipulator remains in the first configuration.

At step 168, if a recognized mounting component is mounted to the manipulator 24, the robotic manipulator is moved to a second configuration. More specifically, if the controller 144 detects a mock instrument mounted to the insertion spar 100, the controller generates an override command to unlock the robotic manipulator 24 from the safety configuration. The controller generates a further command to permit the robotic manipulator 24 to move from the safety configuration to a second configuration, such as a predetermined collapsed configuration of FIG. 4 or a floating configuration. In one alternative, an operator may manually collapse the insertion spar by activating the clutch button 103. The commands generated by the controller in response to detecting a recognized mounting component may be based upon identification information received about the mounting component. For example, information identifying the length of the mounting component may be used to determine a suitable collapsed configuration that does not interfere with other components of the insertion spar.

In an alternative embodiment, a method of controlling a robotic surgical system may include detecting if a recognized component has been mounted to a robotic manipulator. The component may be, for example, an instrument or a cannula. If the mounted component is recognized, the controller retrieves information about the component from, for example, the component itself or databases accessible by the computer system. Responsive to receiving the stored information about the mounted component, the controller generates a command to move the robotic manipulator to predetermined configuration or initiate a predetermined behavior associated with the mounted component. The predetermined configuration or behavior may be, for example, a service pose or a diagnostic mode.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. A method comprising:
    generating a command to move a surgical robotic manipulator to a predetermined safety configuration;
    locking the robotic manipulator in the safety configuration in response to receiving the command;
    detecting if a mock instrument has been mounted on the robotic manipulator when the robotic manipulator is in the safety configuration; and
    if the mock instrument is detected, then generating an override command to unlock the robotic manipulator from the safety configuration.

2. The method of claim 1 wherein the robotic manipulator includes a telescoping insertion spar.

3. The method of claim 2 wherein locking the robotic manipulator in the safety configuration includes arranging the telescoping insertion spar in an expanded configuration.

4. The method of claim 2 further comprising:
    in response to receiving the override command, arranging the telescoping insertion spar in a predetermined collapsed configuration.

5. The method of claim 2 further comprising:
    in response to receiving the override command, permitting the telescoping insertion spar to be moved by operator control.

6. The method of claim 2 wherein the mock instrument includes a distal portion and the insertion spar includes a distal end and wherein the distal portion of the mock instrument is positioned proximally of the insertion spar distal end when the insertion spar is in a collapsed configuration.

7. The method of claim 1 wherein detecting the mock instrument includes identifying information associated with the mock instrument and wherein the override command is responsive to the identified information.

8. The method of claim 1 wherein detecting the mock instrument includes receiving information transmitted from the mock instrument.

9. The method of claim 1 further comprising:
    detecting if the mock instrument has been removed from the robotic manipulator; and
    if the mock instrument has been removed from the robotic manipulator, generating a command to move the surgical robotic manipulator to the predetermined safety configuration.

10. The method of claim 1 further comprising:
    permitting the unlocked robotic manipulator to move to a collapsed configuration; and
    detecting that a cannula has been docked to the surgical robotic manipulator after the robotic manipulator is moved to the collapsed configuration.

11. A robotic surgical system comprising:
    a surgical robotic manipulator;
    a mock instrument adapted to mount to the robotic manipulator; and
    a control system adapted to
        generate a command to lock the robotic manipulator in a predetermined safety configuration;
        detect if the mock instrument is mounted to the robotic manipulator;
        generate a command to unlock the robotic manipulator from the safety configuration if the mock instrument is detected; and
        generate a command to allow the unlocked robotic manipulator to move to a second configuration.

12. The system of claim 11 wherein the surgical robotic manipulator includes a telescoping insertion spar including a plurality of movably coupled links.

13. The system of claim 12 wherein the predetermined safety configuration is an expanded configuration of the telescoping insertion spar.

14. The system of claim 12 further comprising moving the unlocked robotic manipulator to the second configuration, wherein the second configuration is a predetermined collapsed configuration of the telescoping inserting spar.

15. The system of claim 12 wherein the second configuration is an operator controlled configuration of the telescoping insertion spar.

16. The system of claim 12 further comprising a cannula mounted to the surgical robotic manipulator, wherein the mock instrument has a distal end positioned proximally of a distal opening of the cannula when the insertion spar is in a collapsed configuration.

17. The system of claim 11 wherein the mock instrument includes a memory structure configured to store information about the mock instrument.

18. The system of claim 17 wherein the memory structure further comprises a transmitter.

19. The system of claim 17 wherein the control system includes a sensor adapted to retrieve the stored information for use in generating the command to move the unlocked robotic manipulator to a second configuration.

20. A method of controlling a surgical robotic system comprising:
    detecting if a mock instrument has been mounted to a robotic manipulator of the robotic system;
    responsive to the detection of a mock instrument; receiving information about the mock instrument; and
    responsive to the received information, generating a command to move the robotic manipulator to a predetermined configuration.

21. The method claim 20 further comprising:
    responsive to the received information, generating a command to unlock the robotic manipulator from a safety configuration.

22. The method of claim 20 further comprising associating the received information with stored information to formulate the command to move the robotic manipulator to a predetermined configuration.

* * * * *